United States Patent [19]

Enhsen et al.

[11] Patent Number: 5,428,182

[45] Date of Patent: Jun. 27, 1995

[54] BILE ACID DERIVATIVES, PROCESS FOR THEIR PREPARATION AND USE OF THESE COMPOUNDS AS PHARMACEUTICALS

[75] Inventors: Alfons Enhsen, Büttelborn; Heiner Glombik, Hofheim am Taunus; Werner Kramer, Mainz; Günther Wess, Erlensee, all of Germany

[73] Assignee: Hoechst Aktiengesellschaft, Frankfurt am Main, Germany

[21] Appl. No.: 74,753

[22] Filed: Jun. 10, 1993

[30] Foreign Application Priority Data

Jun. 12, 1992 [DE] Germany ............ 42 19 274.9

[51] Int. Cl.$^6$ ............ C07J 51/00
[52] U.S. Cl. ............ 552/509
[58] Field of Search ............ 552/509

[56] References Cited

U.S. PATENT DOCUMENTS

| | | | |
|---|---|---|---|
| 2,931,817 | 4/1960 | Gash et al. | 552/509 |
| 3,663,579 | 5/1972 | Stache | 260/397.4 |
| 3,916,002 | 10/1975 | Taubert et al. | 260/397.4 |
| 4,002,747 | 1/1977 | van der Vies | 552/509 |

FOREIGN PATENT DOCUMENTS

0489423A1 6/1992 European Pat. Off.

*Primary Examiner*—Johann Richter
*Assistant Examiner*—Kimberly J. Kestler
*Attorney, Agent, or Firm*—Finnegan, Henderson, Farabow, Garrett & Dunner

[57] ABSTRACT

Bile acid derivatives of the formula I $$Z(X-GS)n$$

in which GS, X, Z and n have the meanings indicated in the specification, and a process for the preparation of these compounds are described. The compounds are pharmacologically active and can, therefore, be used as pharmaceuticals, in particular as a hypolipidemic.

8 Claims, No Drawings

BILE ACID DERIVATIVES, PROCESS FOR THEIR PREPARATION AND USE OF THESE COMPOUNDS AS PHARMACEUTICALS

DESCRIPTION

Bile acids are synthesized from cholesterol in the liver in several enzymatic steps. They are stored in the gall bladder, from which they are secreted into the small intestine with the bile. There they fulfil important physiological functions during the digestive process, e.g. as cofactors or pancreatic lipases and as natural detergents in the absorption of fats and fat-soluble vitamins. By means of active and passive transport processes, the greatest part of the bile acids returns to the liver from the small intestine via the portal artery blood.

Bile acid-binding polymers have been employed as therapeutics for a relatively long time. They are used in disorders in which inhibition of bile acid reabsorption is desirable. Thus, if the cholesterol blood level is increased, an increased synthesis of bile acids from cholesterol in the liver can be induced by reduction of the bile acids in the enterohepatic circulation. This leads to increased LDL cholesterol absorption from the blood in the liver and to accelerated LDL catabolism. The effect achieved is a reduction in the atherogenic LDL cholesterol in the blood.

The polymers used for this purpose as pharmaceuticals, e.g. cholestyramine or colestipol, have very high daily doses of 12 to 30 g. Besides the high dosage, flavor and odor make acceptance difficult for patient and physician.

Said polymers have side effects because of their selectivity, which is too low. They show excessively high binding rates to vitamins and simultaneously administered pharmaceuticals, and in addition they change the qualitative bile acid composition in the bile. These properties are manifested in various gastrointestinal disorders (e.g. constipation, steatorrhoea), avitaminoses and increased risk of cholelithiasis.

Surprisingly, bile acid derivatives have now been found which do not have said disadvantages.

The invention therefore relates to bile acid derivatives of the formula (I), (I) $Z(-X-GS)_n$ in which
GS is a bile acid radical or modified bile acid radical,
X is a bridge group or a covalent bond, GS being bonded via X in any desired manner,
Z is a central bridge group and n is three or four.

A modified bile acid radical GS is understood as meaning a bile acid derivative in the form of the free acid or ester, in the form of amides and in the salts form, and also bile acid radicals derivatized on the alcohol groups and dimeric bile acid derivatives, in the case of the latter the bile acid derivatives being bonded to one another directly or via a linker. Suitable dimeric bile acid derivatives are described e.g. in EP-A-0 489 423 (corresponding to U.S. patent application Ser. No. 07/802 413).

Linkage of GS via X to Z can take place in principle via all rings. Linkage via ring A is preferred.

GS is preferably a radical of the formula II

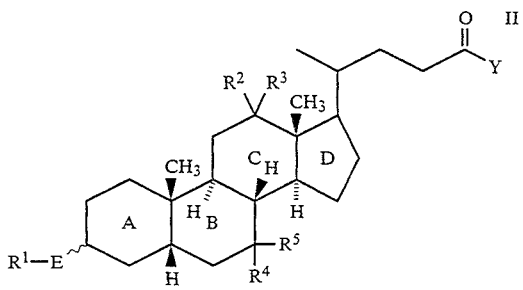

in which
E is a single bond, oxygen or NH,
Y is a free valency for bonding the group X or has the following meanings —OL, —NHL, —NL$_2$, an amino acid bonded via the amino group or aminosulfonic acid, such as e.g.

—NHCH$_2$—CO$_2$H,  —NH—CH$_2$CH$_2$—SO$_3$H,

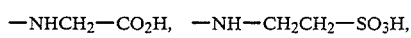

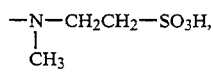   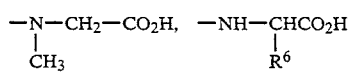

and their (C$_1$–C$_4$)-alkyl esters and alkali metal and alkaline earth metal salts, —OCat, where Cat is a cation such as e.g. an alkali metal or alkaline earth metal ion or else a quaternary ammonium ion and
where L is
H, an alkyl or alkenyl radical having up to 10 carbon atoms, which is branched or unbranched, a cycloalkyl radical having 3 to 8 carbon atoms, a phenyl radical which is unsubstituted or substituted 1 to 3 times by F, Cl, Br, (C$_1$–C$_4$)-alkyl or (C$_1$–C$_4$)-alkoxy,
a benzyl radical, which is unsubstituted or substituted 1 to 3 times by F, Cl, Br, (C$_1$–C$_4$)-alkyl or (C$_1$–C$_4$)-alkoxy,
and R$^6$ is methyl, isopropyl, isobutyl, 2-butyl, benzyl, 4-hydroxybenzyl, hydroxymethyl, 1-hydroxyethyl, H$_3$CSCH$_2$CH$_2$—, HO$_2$CCH$_2$—, HOCCH$_2$CH$_2$—, or
Y is a free valency for bonding a further bile acid radical or modified bile acid radical via ring A thereof, the bonding taking place via a linker having the meaning of X,
R$^1$ is a free valency for bonding the group X or H, an alkyl radical or alkenyl radical having up to 10 carbon atoms, which is branched or unbranched, a cycloalkyl radical having 3 to 8 carbon atoms, a phenyl radical which is unsubstituted or substituted 1 to 3 times by F, Cl, Br, ((C$_1$–C$_4$)-alkyl or (C$_1$–C$_4$)-alkoxy, —NH$_3^\oplus$, —OPO$_3^\ominus$,
a benzyl radical, which is unsubstituted in the ring or substituted 1 to 3 times by F, Cl, Br, (C$_1$–C$_4$)-alkyl, (C$_1$–C$_4$)-alkoxy, —NH$_3^\oplus$, —OPO$_3^\ominus$ or phenyl, which in turn can be substituted 1 to 3 times by F, Cl, Br, (C$_1$–C$_4$)-alkyl or (C$_1$–C$_4$)-alkoxy, —NH$_3^\oplus$, —OPO$_3^\ominus$,
a biphenylmethyl radical which is unsubstituted or substituted 1 to 3 times by F, Cl, Br, (C$_1$–C$_4$)-alkyl, (C$_1$–C$_4$)-alkoxy, —NH$_3^\oplus$, —OPO$_3^\ominus$,
a triphenylmethyl radical which is unsubstituted or substituted 1 to 3 times by F, Cl, Br, (C$_1$–C$_4$) -alkyl or (C$_1$–C$_4$)-alkoxy, —NH$_3^\oplus$, —OPO$_3^\ominus$, a 1- or 2-naphthylmethyl radical, which is unsubstituted or substituted 1 to 3 times by F, Cl, Br, ($C_1$-$C_4$)-alkyl or ($C_1$-$C_4$)-alkoxy, —$NH_3^{\oplus}$, —$OPO_3^{\ominus}$, a 9-fluorenyl radical which is unsubstituted or substituted 1 to 3 times by F, Cl, Br, , ($C_1$-$C_4$)-alkyl or ($C_1$-$C_4$)-alkoxy, —$NH_3^{\oplus}$, —$OPO_3^{\ominus}$, a 2-, 3- or 4-pyridyl radical,

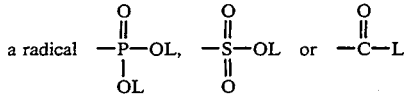

where L has the abovementioned meaning, $R^2$ to $R^5$, where $R^2$ and $R^3$ or $R^4$ and $R^5$ in each case together are the oxygen of a carbonyl group, or individually and in each case independently of one another are

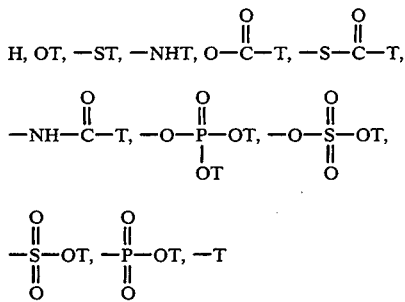

where T is hydrogen, alkyl having up to 10 carbon atoms, cycloalkyl having 3 to 8 carbon atoms, phenyl or tetrahydropyranyl, X is preferably a single bond or a group of the formula III

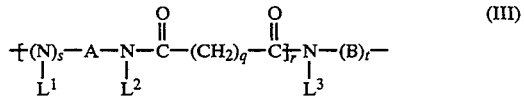 (III)

where
A is an alkylene chain which is branched or unbranched and can be optionally interrupted by —O—, —S— or phenylene in the chain, where the linkage

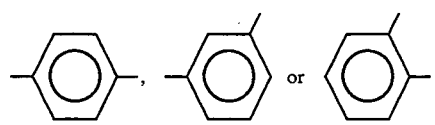

takes place and the chain altogether comprises 2 to 12, preferably 2 to 6, chain members p, B is an alkylene chain, which is branched or unbranched and can be optionally interrupted by —O—, —S— or phenylene in the chain where the linkage

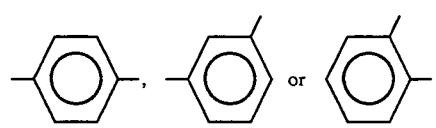

takes place the chain altogether contains 2 to 18, preferably 2 to 12, chain members n, $L^1$, $L^2$ and $L^3$ are identical or different and have the meaning of L, but in particular are hydrogen, $C_1$-$C_4$-alkyl or benzyl, and q is 0 to 5,
r is 0 or 1,
s is 0 or 1 and
t is 0 or 1.

The bile acid derivative of the formula (II) is preferably α- or β-linked to X in the 3-position.

The central bridge group Z has 3 to 4

which are bonded to X-GS via NH groups.

Z is preferably an open-chain alkyl radical having up to 20 carbon atoms, the alkyl radical being straight-chain or branched and optionally being interrupted with up to 6 ether bridges, a cycloalkyl radical having 3 to 8 carbon atoms or a phenyl radical, said radicals having 3 to 4

and being bonded to

X via —NH and where said radicals can be substituted by e.g. $NH_2$, $NO_2$, $C_1$-$C_3$-alkyl, preferably methyl, or phenyl.

If the bridge groups can have various steric arrangements, then all possible arrangements are included by the above definition of Z.

The linkage of GS to X is preferably α or β in the 3-position (ring A).

Preferred compounds of the formula I are those in which GS is a radical of the formula II and X is NH or a hydrocarbon chain having 2 to 8 carbon atoms, which is interrupted by 1 to 3 oxygen atoms or 1 to 2

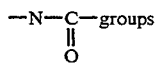

and bonding to GS takes place via —O—, —NH— or —$CH_2$—.

The invention furthermore relates to a process for the preparation of compounds of the formula I, which comprises reacting activated carboxylic acid derivatives with suitable amines with the formation of an amide bond.

The carboxylic acid derivatives contain the central bridge group, while the amines contain the group X-GS. The oligocarboxylic acids used are either known from the literature or they are prepared by addition of hydroxy compounds to acrylonitrile and subsequent hydrolysis of the nitrile functions.

Oligocarboxylic acids suitable as the central component are activated e.g. by formation of anhydride or acid chloride. Other exemplary possibilities are activation with a) dicyclohexylcarbodiimide/hydroxybenzotriazole (DCC/HOBT, b) 2-ethoxy-1-ethoxycarbonyl-1,2-dihydroisoquinoline (EEDQ) or c) O-[(cyanoethoxycarbonylmethylene)amino]-N,N,N',N'-tetramethyluronium tetrafluoroborate (TOTU).

Depending on reactivity, the amino bile acid derivatives, which in some cases are also protected, are reacted in a temperature range from $-15°$ to $+75°$ C., preferably in inert solvents such as tetrahydrofuran, dichloromethane, dimethylformamide or ethyl acetate.

The esters of the formula I formed are hydrolyzed by base, in the case of benzyl esters by hydrogenolysis, according to a customary method and can then be converted into the alkali metal salts.

For the preparation of compounds having different radicals on the central component, the reaction sequence "activation" and "condensation" can be carried out several times using various amino bile acid derivatives, e.g. a) anhydride/acid chloride formation, b) 1st condensation, c) activation of remaining free carboxyl groups with DCC/HOBT and d) 2nd condensation.

The compounds of the formula (I) according to the invention have a high affinity for the specific bile acid transport system of the small intestine and inhibit bile acid reabsorption in a concentration-dependent and competitive manner.

Compounds of the formula (I) are themselves not absorbed and thus do not reach the blood circulation. Substantially more selective intervention in the enterohepatic circulation can be made by reversible inhibition. Avitaminoses are not to be expected, Just as little as there is a qualitative change of the bile acid composition in the bile. Using the compounds according to the invention, a controlled decrease in the serum cholesterol level can be achieved without the known side effects being observed. The compounds according to the invention can furthermore be employed for the treatment of liver disorders with cholostasis, since the recirculation of bile acids, which are responsible under cholostasis conditions for hepatocellular damage and necroses, is decreased by the interruption of the enterohepatic circulation.

Because of the high affinity of the compounds according to the invention for the bile acid transport system, very much lower daily doses can be used than with the commercially available polymers; this also leads to a high acceptance for patient and physician.

The compounds have useful pharmacological properties and are therefore particularly suitable as hypolipidemics.

The invention therefore also relates to pharmaceuticals based on compounds of the formula (I) and the use of the compounds as pharmaceuticals, in particular for decreasing the cholesterol level.

The biological testing of the compounds according to the invention was carried out by determining the inhibition of [$^3$H]-taurocholate absorption in brush border membrane vesicles of the rabbit ileum. The inhibition test was carried out as follows:

1. Preparation of brush border membrane vesicles from rabbit ileum.

Brush border membrane vesicles from the intestinal cells of the small intestine were prepared by the so-called $Mg^{2+}$ precipitation method. Male New Zealand rabbits (2 to 2.5 kg body weight) were sacrificed by intravenous injection of 0.5 ml of an aqueous solution of 2.5 mg of tetracaine HCl, 100 T 61 ® and 25 mg of mebezonium iodide. The small intestine was removed and rinsed with ice-cold physiological saline solution. The terminal 7/10 of the small intestine (measured in the oral-rectal direction, i.e. the terminal ileum, which contains the active $Na^+$-dependent bile acid transport system) were used for the preparation of the brush border membrane vesicles. The intestines were frozen under nitrogen at $-80°$ C. in plastic bags. For the preparation of the membrane vesicles, the frozen intestines were thawed at 30° C. in a water bath. The mucosa was scraped off and suspended in 60 ml of ice-cold 12 mM tris/HCl buffer (pH 7.1)/300 mM mannitol, 5 mM EGTA/10 mg/l of phenylmethylsulfonyl fluoride/1 mg/l of trypsin inhibitor from soybeans (32 U/mg)/0.5 mg/l of trypsin inhibitor from bovine lung (193 U/mg)/5 mg/l of bacitracin. After dilution to 300 ml with ice-cold distilled water, the suspension was homogenized using an Ultraturrax (18-rod, IKAWerk Staufen, FRG) for 3 minutes at 75% maximum power with ice-cooling. After addition of 3 ml of 1M $MgCl_2$ solution (final concentration 10 mM), the homogenate was allowed to stand at 0° C. for exactly 1 minute. As a result of addition of $Mg^{2+}$, the cell membranes aggregate and precipitate with the exception of the brush border membranes. After centrifugation at $3000 \times g$ for 15 minutes (5000 rpm, SS-34 rotor), the precipitate is discarded and the supernatant which contains the brush border membranes is centrifuged at $267,000 \times g$ for 30 minutes (15,000 rpm, SS-34 rotor). The supernatant was discarded and the precipitate was rehomogenized in 60 ml of 12 mM tris/HCl buffer (pH 7.1)/60 mM mannitol/5 mM EGTA using a Potter Elvejhem homogenizer (Braun Melsungen, 900 rpm, 10 strokes). After addition of 0.1 ml of 1M $MgCl_2$ solution and an incubation time of 15 minutes at 0° C., centrifugation was once more carried out at $3000 \times g$ for 15 minutes. The supernatant was then centrifuged again at $46,000 \times g$ (15,000 rpm, SS-34 rotor) for 30 minutes. The precipitate was taken up in 30 ml of 10 mM tris/hepes buffer (pH 7.4)/300 mM mannitol and homogeneously resuspended at 1000 rpm by 20 strokes in a Potter Elvejhem homogenizer. After centrifugation at $48,000 \times g$ (20,000 rpm, SS-34 rotor) for 30 minutes, the precipitate was taken up in 0.5 to 2 ml of tris/HEPES buffer (pH 7.4)/280mM mannitol (final concentration 20 mg/ml) and resuspended with the aid of a tuberculin syringe having a 27 gauge needle. The vesicles were either used immediately after preparation for transport investigations or stored in liquid nitrogen at $-196°$ C. in 4 mg portions.

2Inhibition of the $Na^+$-dependent [$^3$H]taurocholate absorption in brush border membrane vesicles of the ileum.

The absorption of substrates in the brush border membrane vesicles described above was determined by means of the so-called membrane filtration technique. 10 µl of the vesicle suspension (100 µg of protein) were pipetted as drops onto the wall of a polystyrene incubation tube (11×70 mm) which contained the incubation medium with the appropriate ligands (90 µl). The incubation medium contained 0.75 µl = 0.75 µCi of [$^3$H(G)]-taurocholate (specific activity: 2.1 Ci/mMol)/0.5 µl of 10 mM taurocholate/8.75 µl of sodium transport buffer (10 mM tris/HEPES (pH 7.4)/100 mM mannitol/100 mM NaCl) (Na-T-B) or 8.75 µl of potassium transport buffer (10 mM tris/hepes (pH 7.4)/100 mM mannitol/100 mM KCl) (K-T-B) and 80 µl of the inhibitor solution concerned, depending on the experiment, dissolved in Na-T buffer or K-T buffer. The incubation medium was filtered by means of a polyvinylidene fluoride membrane filter (SYHV LO 4NS, 0.45 µm, 4 mm φ, Millipore, Eschborn, FRG). The transport measurement was started by mixing the vesicles with the incubation medium. The concentration of taurocholate in the incubation batch was 50 µM. After the desired incubation time (customarily 1 minute), transport was stopped by addition of 1 ml of ice-cold stop solution (10 mM tris/HEPES (pH 7.4)/150 mM KCl. The resulting mixture was immediately filtered with suction through a membrane filter made of cellulose nitrate (ME 25, 0.45 μm, 25 mm diameter, Schleic2her & Schuell, Dassell, FRG) under a vacuum of 25 to 35mbar. The filter was washed with 5 ml of ice-cold stop solution.

To measure the absorption of the radiolabelled taurocholates, the membrane filter was dissolved using 4 ml of the scintillator Quickszint 361 (Zinsser Analytik GmbH, Frankfurt, FRG) and the radioactivity measured by liquid scintillation measurement in a TriCarb 2500 measuring apparatus (Canberra Packard GmbH, Frankfurt, FRG). After calibration of the apparatus with the aid of standard samples and after correction for possible chemiluminescence, the measured values were obtained as dpm (decompositions per minute).

The control values were in each case determined in Na-T-B and K-T-B. The difference between the absorption in Na-T-B and K-T-B gave the proportion of $Na^+$-dependent transport. The $IC_{50}Na^+$ was designated as that concentration of inhibitor at which the proportion of $Na^+$-dependent transport was inhibited by 50%, relative to the control.

The table shows measurement values of the inhibition of [$^3$H]-taurocholate absorption in brush border membrane vesicles of rabbit ileum. The quotients of the $IC_{50}$ or $IC_{50Na}$, values of the taurochenodeoxycholate (TCDC) investigated as a standard in each vesicle preparation and the respective substance are indicated.

| Substance from example | $IC_{50}$ (TCDC) $IC_{50}$ (Substance) | $IC_{50Na}$ (TCDC) $IC_{50Na}$ (Substance) |
| --- | --- | --- |
| 7 | 0.29 | 0.34 |
| 10 | 0.24 | 0.26 |
| 11 | 0.29 | 0.36 |
| 16 | 0.37 | 0.31 |
| 18 | 0.85 | 0.76 |
| 20 | 0.43 | 0.86 |
| 21 | 0.29 | 0.59 |
| 31 | 1.26 | 0.93 |
| 33 | 0.77 | 1.04 |
| 45 | 0.32 | 0.23 |
| 47 | 0.24 | 0.23 |

The invention furthermore relates to the use of compounds according to the invention for the preparation of a medicine.

For this purpose, the compounds of the formula I are dissolved or suspended in pharmacologically acceptable solvents, such as mono- or polyhydric alcohols, such as e.g. ethanol or glycerol, in triacetin, oils such as e.g. sunflower oil, fish liver oil, ethers, such as e.g. diethylene glycol dimethyl ether or else polyethers such as e.g. polyethylene glycol, or else in the presence of other pharmacologically acceptable polymer excipients, such as e.g. polyvinylpyrrolidone, or other pharmaceutically acceptable additives such as starch, cyclodextrin or polysaccharides. The compounds according to the invention can also be given in combination with other pharmaceutical substances.

The compounds of the formula I are administered in various dose forms, preferably orally in the form of tablets, capsules or liquids. The daily dose varies depending on the body weight and constitution of the patient in the range from 3 mg to 5000 mg, but preferably in the dose range 10 to 1000 mg.

EXAMPLE 1

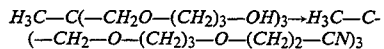

14.5 ml (220 mmol) of acrylonitrile were slowly added dropwise at room temperature to a suspension of 8.0 g (27.2 mmol) of 1,1,1-tris(3-hydroxypropoxymethyl)ethane in 40 ml of dioxane and 0.4 g of 40% aqueous KOH. After 1 h at 40° C., a further 1.0 g of 40% aqueous KOH was added and the mixture was stirred at 70° C. for a further 2 h. After completion of the reaction, 5 ml of 2M HCl were added, the insoluble products were filtered off and the solvent was concentrated. The residue was dissolved in $CH_2Cl_2$, and the solution was dried using $MgSO_4$ and concentrated again. Chromatography on silica gel (cyclohexane/ethyl acetate 1:2) gave 7.4 g (60%, 16.3 mmol) of "Example 1".

$C_{23}H_{39}N_3O_6$ (453), MS (FAB, 3-NBA/LiCl): 460 ($M+Li^+$).

EXAMPLE 2

5.2 g (11.5 retool) of Example 1 were dissolved in 60 ml of methanolic HCl and heated under reflux for 3 h. The precipitate was filtered off and the solvent was concentrated. The residue obtained was heated under reflux in a water separator for 3 h in 50 ml of toluene. The mixture was then concentrated in vacuo. Yield: 4.0 g (63%, 7.2 mmol) of "Example 2".

$C_{28}H_{48}O_{12}$(552), MS (FAB, 3-NBA/LiCl): 559 ($M+Li^+$).

EXAMPLE 3

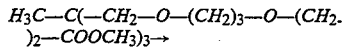

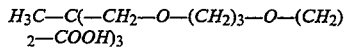

4.0 g (7.2 mmol) of Example 2 were hydrolyzed at room temperature in 40 ml of 2M aqueous NaOH. For working-up, the mixture was acidified with 2M HCl and extracted with ethyl acetate. After drying and concentration of the organic phase, the residue was purified on a short silica gel column ($CHCl_3$/MeOH 4:1).

Yield: 3.0 g ( 5.9 mmol, 82% ) of "Example 3".

$C_{23}H_{42}O_{12}$ (510), MS (FAB, 3-NBA/LiCl): 517 ($M+Li^+$).

EXAMPLE 4

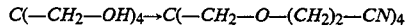

218 g (1.56 mol) of pentaerythritol and 5..3 g (0.13 mol) of NaOH were dissolved in 250 ml of water. 525 ml (8 mol) of acrylonitrile were slowly added dropwise. The reaction was stirred at 50° C. for 12 h. The mixture was then neutralized with HCl and filtered through silica gel (ethyl acetate). Yield: 345 g (0.99 mol, 63%) of "Example 4".

$C_{17}H_{24}N_4O_4$ (348), MS (FAB, 3-NBA/LiCl): 355 ($M'Li^+$).

EXAMPLE 5

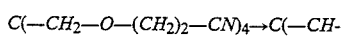
C(—CH₂—O—(CH₂)₂—CN)₄→C(—CH- 
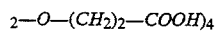
₂—O—(CH₂)₂—COOH)₄

100 g (287 mmol) of Example 5 were heated under reflux for 1 h in 500 ml of concentrated HCl. After cooling, the mixture was saturated with NaCl and extracted with ethyl acetate. After drying and concentration of the organic phase, it was filtered through silica gel (ethyl acetate). Yield: 83.5 g (197 mmol, 69%) of "Example 5. $C_{17}H_{28}O_{12}$ (424), MS (FAB, 3-NBA/-LiCl): 431 (M+Li⁺).

EXAMPLE 6

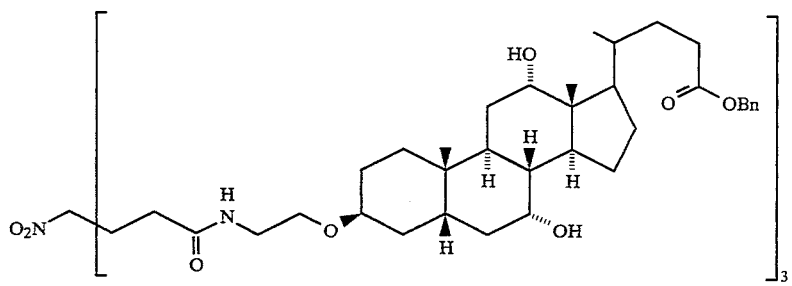

200 mg( 0.72 mmol) of tris(2-carboxyethyl )nitromethane in 20 ml of tetrahydrofuran at 0° C. were treated first with 0.59 ml ( 4.3 mmol ) of triethylamine, then with 0.2 ml (2.1 mmol) of ethyl chloroformate. After 30 min. at 0° C., 1.16 g (2.1 mmol) of benzyl 3β-(2-aminoethoxy)-7α, 12α-dihydroxycholanate in 5 ml of THF were added. After a further 3 h at 0° C. and 2 h at room temperature, the reaction mixture was concentrated and chromatographed on silica gel (CH₂Cl₂/methanol 9:1 ). Yield: 780 mg (0.42 mmol, 59%) of "Example 6".

$C_{109}H_{162}N_4O_{20}$ (1847), MS (FAB, 3-NBA/LiCl): 1854 (M+Li⁺)

EXAMPLE 7

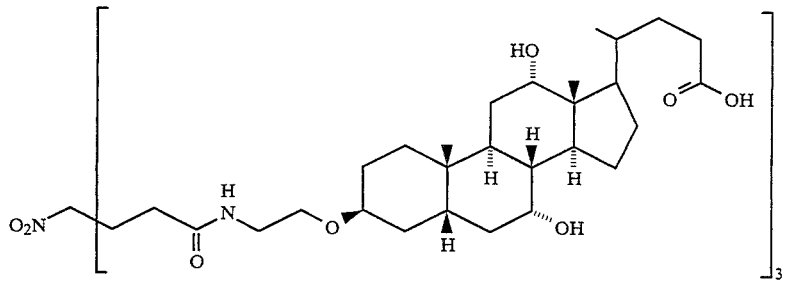

200 mg (0.108 retool) of Example 6 were hydrogenated at normal pressure in 15 ml of methanol in the presence of 10 mg of Pd/C. The catalyst was filtered off and the filtrate was concentrated. 150 mg ( 0. 095 mmol, 88% ) of "Example 7" were obtained.

$C_{88}H_{144}N_4O_{20}$ (1577), MS (FAB, 3-NBA/LiCl): 1584 (M+Li⁺).

EXAMPLE 8

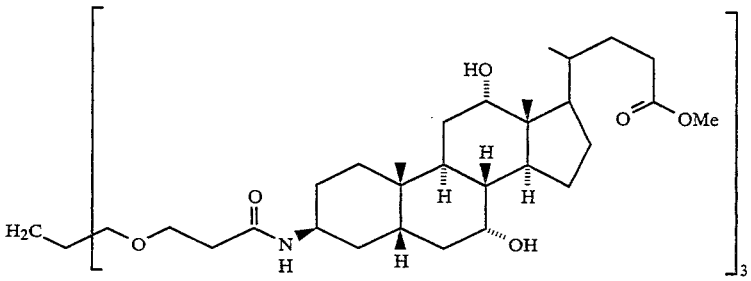

300 mg( 0.59 mmol) of 1,1,1-tris (2-carboxyethoxymethyl) ethane were treated with 0.56 ml (4.0 mmol) of triethylamine and 0.26 ml (2.72 mmol) of ethyl chloroformate in 30 ml of THF at 0° C. After 15 min. at 0° C., 1.8 g (3.52 mmol) of methyl 3β-amino-7α, 12α-dihydroxycholanate in 10 ml of THF were added at −10° C., and the mixture was stirred for 1 h at −10° C. and for 30 min. at room temperature. After concentration of the reaction mixture, the residue was chromatographed on silica gel (ethyl acetate/methanol/triethylamine 5:1:1). Yield: 900 mg ( 5.23 mmol, 89%) of "Example 8".

$C_{89}H_{147}N_3O_{18}$ (1546), MS (FAB, 3-NBA/LiCl): 1.553 (M+Li⁺).

EXAMPLE 9

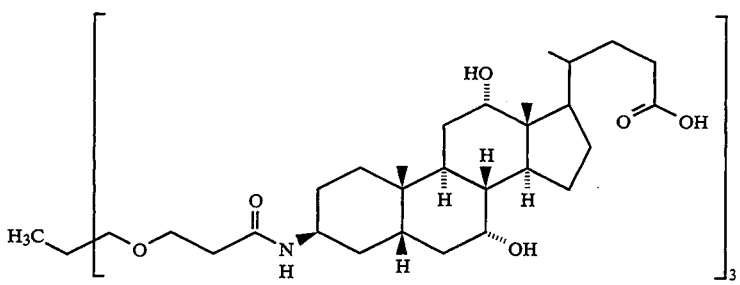

500 mg (0.29 mmol) of Example 8 were hydrolyzed using 2 ml of 1M aqueous NaOH in 10 ml of ethanol. For working-up, water was added and the ethanol was stripped off, and the residue was acidified with HCl and extracted with ethyl acetate. After drying and concentration of the solvent, the residue was chromatographed on silica gel (CHCl$_3$/MeOH 4:1, then 1:1). Yield: 260 mg (0.15 mmol, 53%) of "Example 9".

$C_{86}H_{141}N_3O_{18}$ (1504), MS (FAB, 3-NBA/LiCl): 1511 (M+Li$^+$).

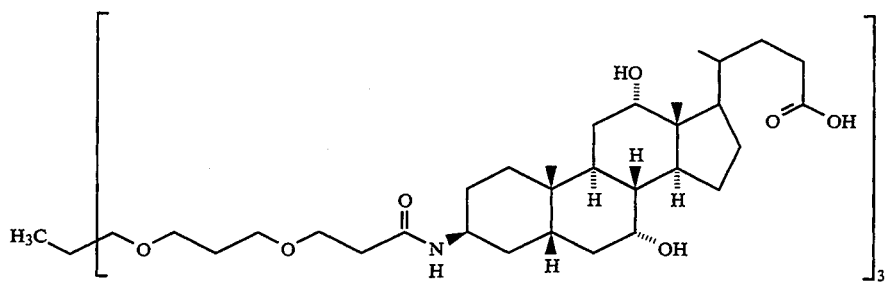

EXAMPLE 10

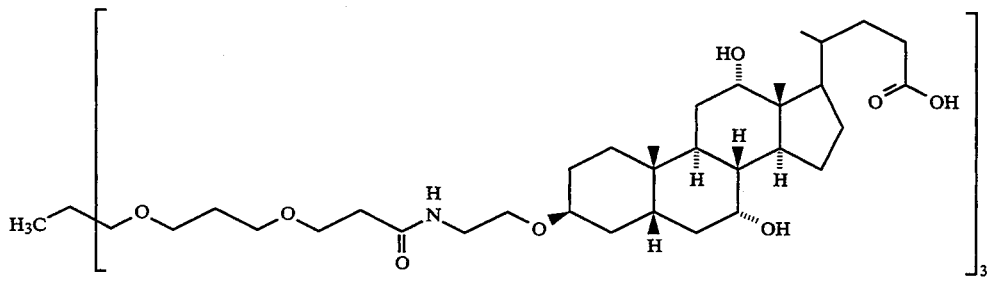

"Example 10" was obtained from 1,1,1-tris(2-carboxyethoxymethyl)ethane and methyl 3β-(2-aminoethoxy)-7α,12α-dihydroxycholanate analogously to Examples 8 and 9.

$C_{92}H_{153}N_3O_{21}$ (1636), MS (FAB, 3-NBA/LiCl): 1643 (M+Li$^+$).

EXAMPLE 11

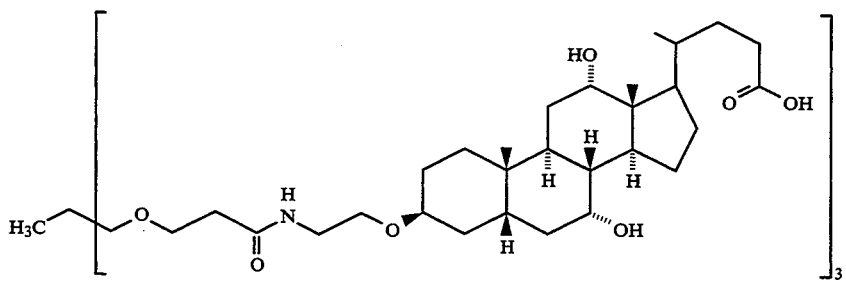

"Example 11" was obtained from Example 3 and 3β-amino-3α, 7α-dihydroxycholanic acid analogously to Examples 8 and 9.

$C_{95}H_{159}N_3O_{21}$ (1678), MS (FAB, 3-NBA/LiCl) 1685 (M+Li$^+$).

EXAMPLE 12

"Example 12" was obtained from Example 3 and methyl 3β-(2-aminoethoxy)-7α,12α-dihydroxycholanate analogously to Examples 8 and 9.

$C_{101}H_{171}N_3O_{24}$ (1810), MS (FAB, 3-NBA/LiCl): 1817 (M +Li$^+$).

EXAMPLE 13

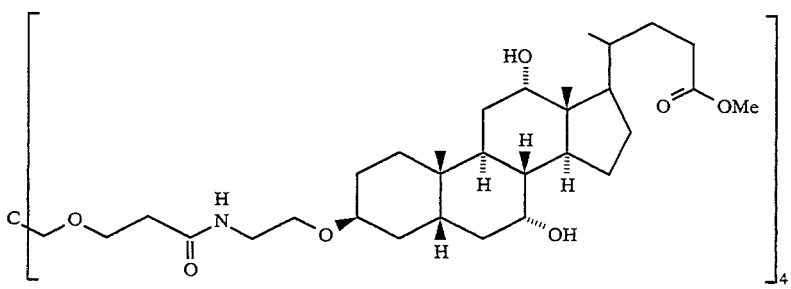

A solution of 0.5 g (1.12 mmol) of Example 5 and 3.0 g ( 6.45 mmol) of methyl 3β-( 2-aminoethoxy)-7α, 12α-cholanate in 20 ml of dry ethyl acetate was treated with 1.36 g (5.50 mmol) of 2-ethoxy-1-ethoxycarbonyl-1,2-dihydroquinoline and the mixture was heated under reflux for 20 h. After completion of the reaction, the solvent was evaporated and the residue was chromatographed on silica gel (CHCl$_3$/methanol 10:1). 1.40 g (0.63 mmol, 54%) of "Example 13" were obtained.

C$_{125}$H$_{208}$N$_4$O$_{28}$ (2213), MS (FAB, 3-NBA/LiCl): 2220 (M+Li$^+$).

EXAMPLE 14

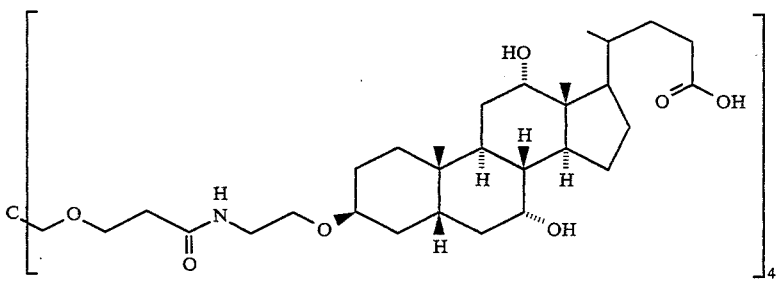

Example 13 was hydrolyzed to Example 14 analogously to the process described for Example 9. The product was purified by chromatography on RP-8 silica gel using methanol/water 85:5 as the eluent. C$_{121}$H$_{220}$N$_4$O$_{28}$ (2157), MS (FAB, 3-NBA/LiCl): 2164 (M+Li$^+$).

EXAMPLE 15

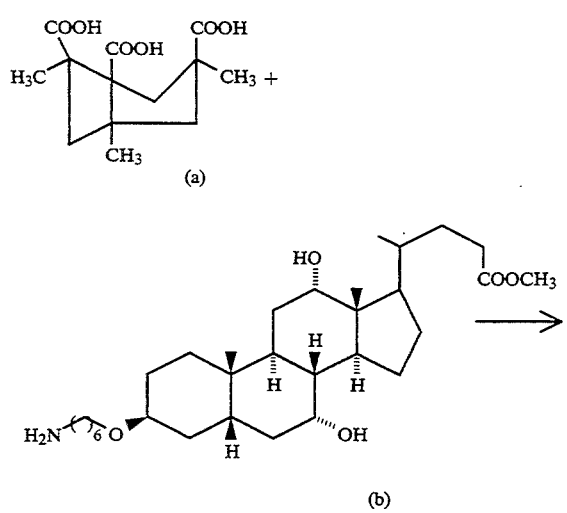

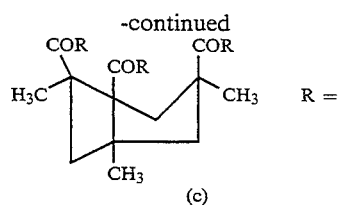

6.8 g ( 0. 033 tool ) of dicyclohexylcarbodiimide (DCC) are added at 0° C. to a solution of 2.58 g (0.01 tool) of Kemp's triacid (a), 16.5 g (0.03 tool) of amine (b) and 4.46 g (0.033 mol) of hydroxybenzotriazole (HOBT) in 300 ml of THF. The solution is stirred for 30 min. at 0° C. and then for 20 h at room temperature. To complete the reaction, 1.12 g of HOBT and 1.7 g of DCC are added and the mixture is again stirred for 20 h. The precipitate formed is then filtered off, the filtrate is concentrated, the residue is taken up with ethyl acetate and the solution is washed successively with 2N citric acid, water, satd. NaHCO$_3$ solution and water. The residue obtained after drying and concentration is purified by chromatography (SiO$_2$; ethyl acetate/methanol 10:1). 16.8 g (95%) of product (c), "Example 15", are obtained.

C$_{105}$H$_{177}$N$_3$O$_{18}$ (1768), MS (FAB, 3-NBA/LiCl): 1775 (M+Li$^+$).

EXAMPLE 16

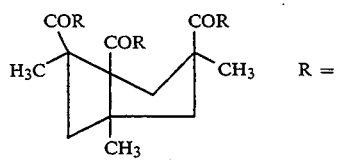
R =

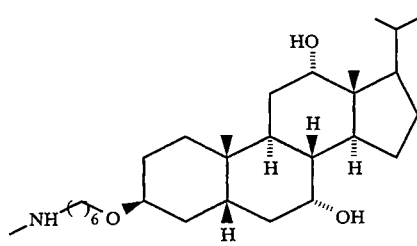

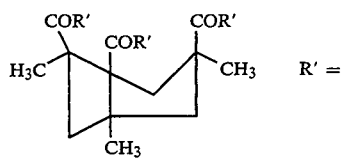
R' =

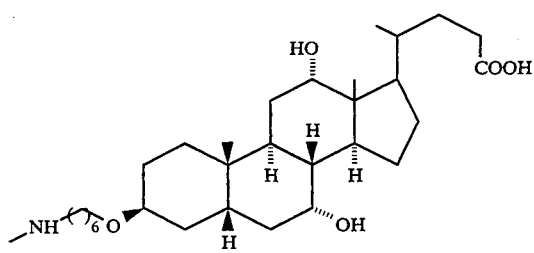

16.8 g of Example 15 were dissolved in 200 ml of dioxane and treated at 0° C. with 100 ml of half-concentrated sodium hydroxide solution. After stirring at room temperature for 2 h, the mixture was [lacuna] with 300 ml of water and stirred overnight at room temperature. After reaction was complete, the mixture was diluted with a further 500 ml of water, acidified with dilute hydrochloric acid and stirred in an ice bath for 1 h. The resulting precipitate was filtered off with suction, washed with water, recrystallized from ethanol/water and dried in vacuo. 15.1 g (92%) of "Example 16" were obtained in microcrystalline form.

$C_{102}H_{171}N_3O_{18}$ (1727), MS (FAB, AcOH, NBA): 1728 (M +H$^+$); m.p.: 168° C.

EXAMPLE 17

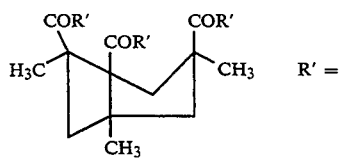
R' =

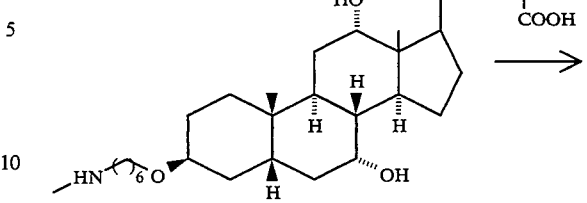

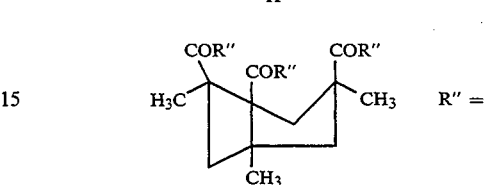
R'' =

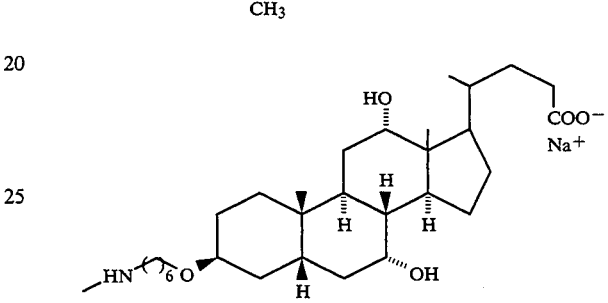

345 mg (0.2 mmol) of Example 16 were dissolved in 5 ml of dry methanol and treated with 1 ml of 0.2N methanolic sodium hydroxide solution. The sodium salt was precipitated by adding about 50 ml of dry ether and stirring at 0° C. for 1 h, filtered off with suction, washed with cold ether and dried in vacuo. 310 mg (87%) of "Example 17" were obtained.

$C_{102}H_{168}N_3Na_3O_{18}$ (1792), MS (FAB, NBA) 1728 (M-3Na$^+$+4H$^+$); m.p.=201°-203° C.

The following substances were prepared from the corresponding carboxylic acids and amines analogously to "Example 15" and "Example 16":

EXAMPLE 18

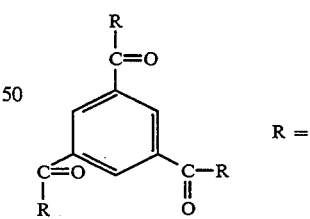
R =

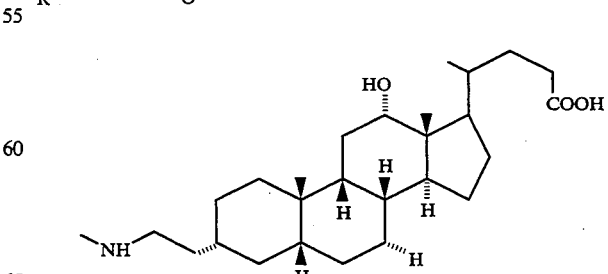

$C_{87}H_{135}N_3O_{15}$ (1462), MS (FAB, 3-NBA): 1463 (M+H$^+$)

EXAMPLE 19
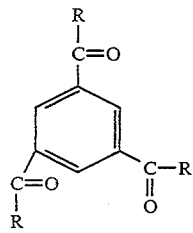
R =
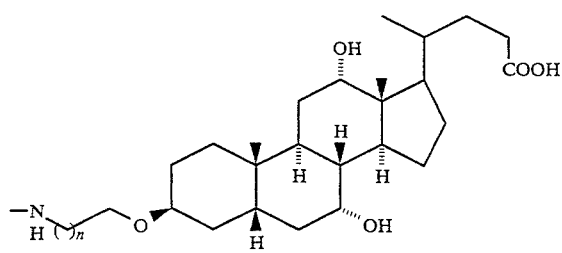
n = 1
$C_{87}H_{135}N_3O_{18}$ (1510), MS (FAB, 3-NBA): 1511 (M+H$^+$)
EXAMPLE 20
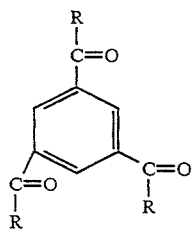
R =
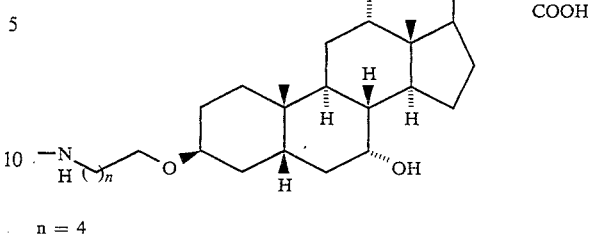
n = 4
$C_{96}H_{153}N_3O_{18}$ (1636), MS (FAB, 3-NBA): 1637 (M+H$^+$)
EXAMPLE 21
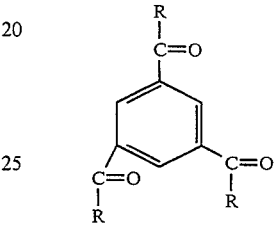
R =
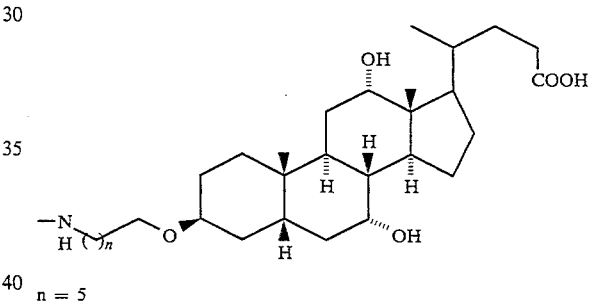
n = 5
$C_{99}H_{159}N_3O_{18}$ (1678), MS (FAB, 3-NBA)=1679 (M+H$^+$)
EXAMPLE 22
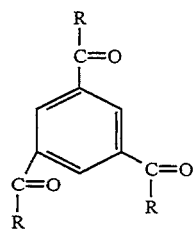
R =

-continued
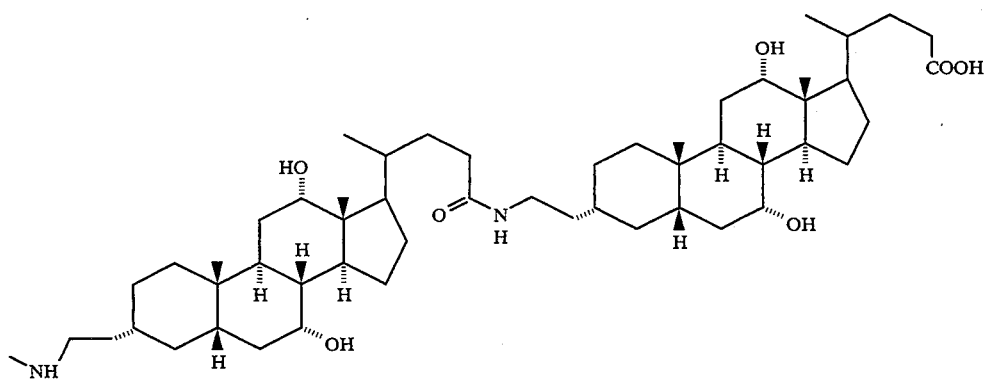
$C_{165}H_{264}N_6O_{24}$ (2714), MS (FAB, 3-NBA, AcOH): 2737 (M+Na+)
EXAMPLE 23
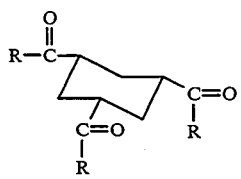
R =
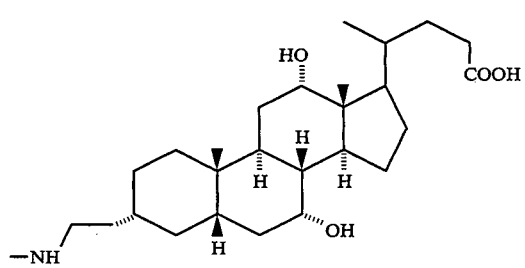
$C_{87}H_{141}N_3O_{15}$ (1468), MS (FAB, 3-NBA): 1469 (M+H+)
EXAMPLE 24
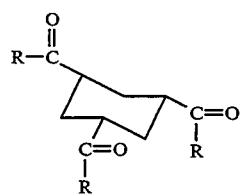
R =
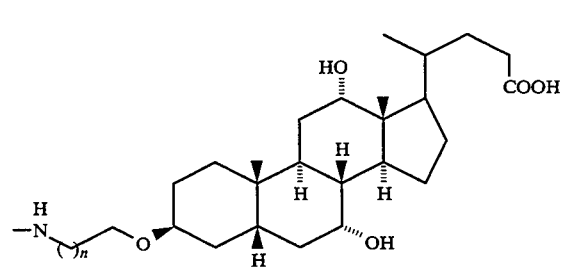
n = 1
$C_{87}H_{141}N_3O_{18}$ (1516), MS (FAB, 3-NBA): 1517 (M+H+)
EXAMPLE 25
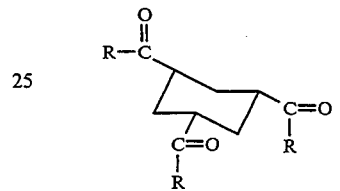
R =
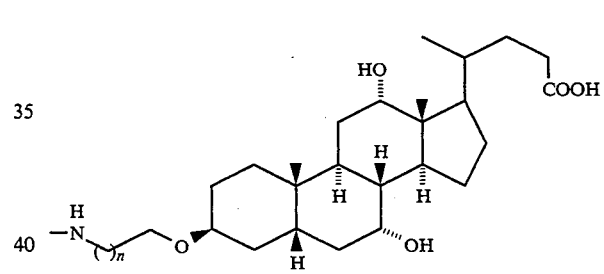
n = 5
$C_{99}H_{165}N_3O_{18}$ (1684), MS (FAB, 3-NBA): 1685 (M+H+)
EXAMPLE 26
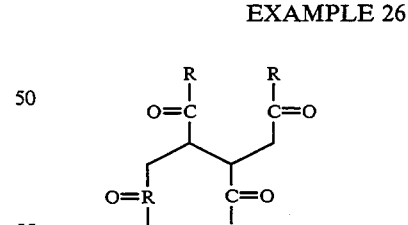
R =
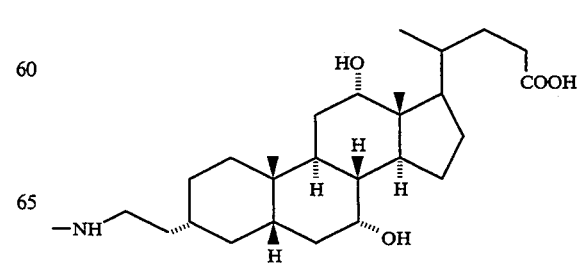

$C_{112}H_{182}N_4O_{20}$ (1903) MS (FAB, 3-NBA): 1904 (M+H+)
EXAMPLE 27
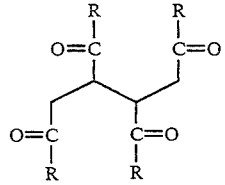
R =
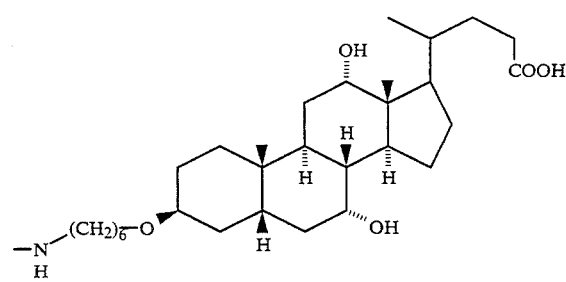
$C_{128}H_{214}N_4O_{24}$ (2192), MS (FAB, 3-NBA): 2193 (M+H+)
EXAMPLE 28
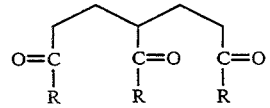
R =
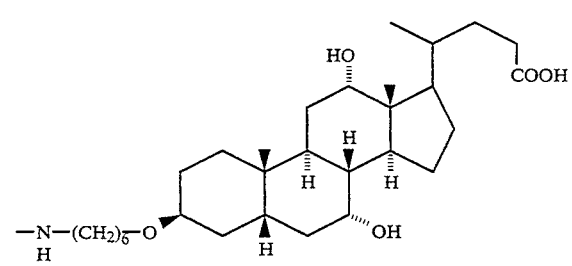
$C_{98}H_{165}N_3O_{18}$ (1672), MS (FAB, 3-NBA): 1673 (M+H+)
EXAMPLE 29
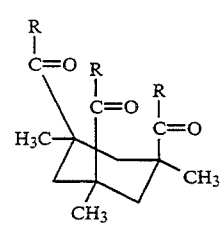
R =
-continued
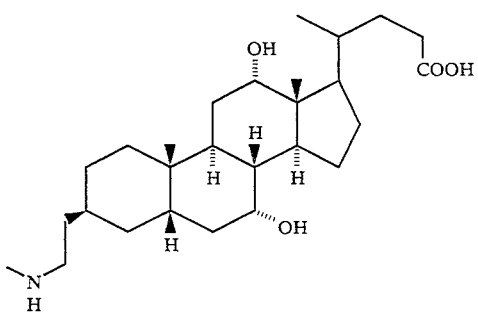
$C_{90}H_{147}N_3O_{15}$ (1510), MS (FAB, 3-NBA): 1511 (M+H+)
EXAMPLE 30
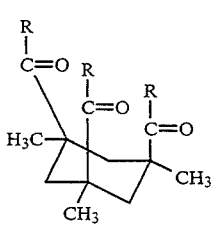
R =
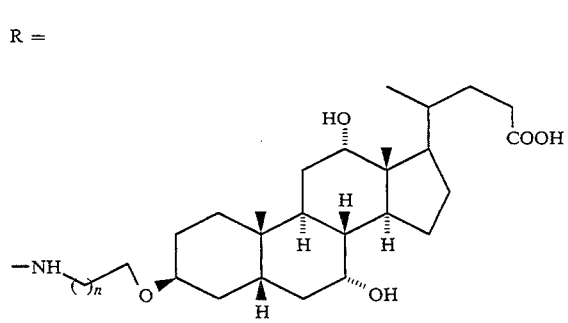
n = 1
$C_{90}H_{147}N_3O_{18}$ (1558), MS (FAB, 3NBA): 1559 (M+H+)
EXAMPLE 31
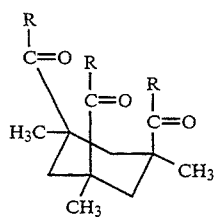
R =
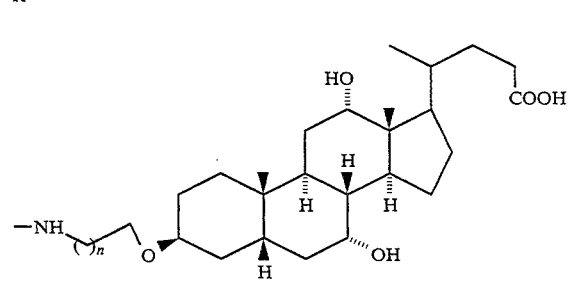

n = 4
C$_{99}$H$_{165}$N$_3$O$_{18}$ (1684), MS (FAB, 3-NBA): 1685 (M+H$^+$)
EXAMPLE 32
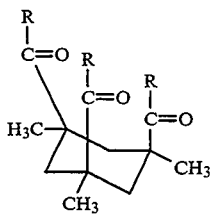
R =
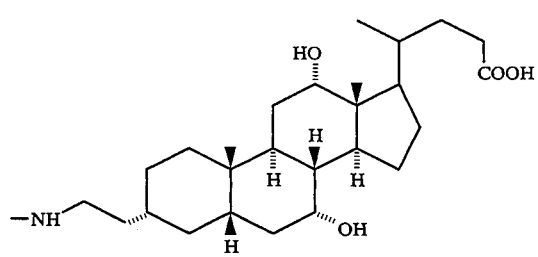
C$_{90}$H$_{147}$N$_3$O$_{15}$ (1510), MS (FAB, 3-NBA): 1511 (M+H$^+$)
EXAMPLE 33
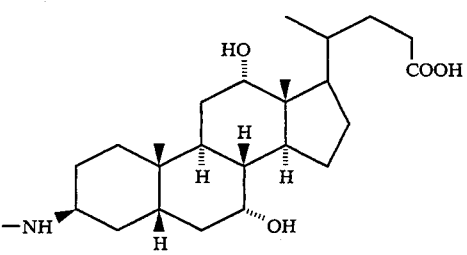
R =
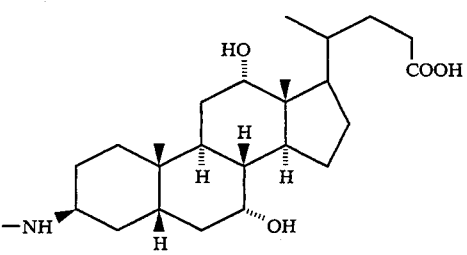
C$_{84}$H$_{135}$N$_3$O$_{15}$ (1426), MS (FAB, 3-NBA): 1427 (M+H$^+$)
EXAMPLE 34
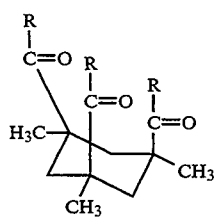
R =
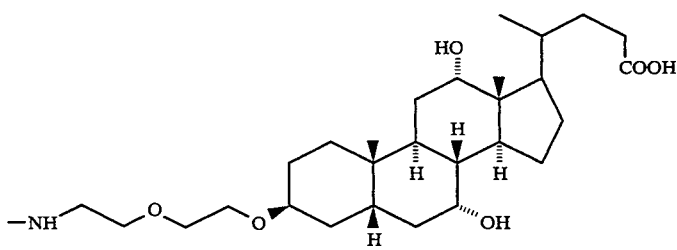
C$_{96}$H$_{159}$N$_3$O$_{21}$ (1690), MS (FAB, 3-NBA): 1713 (M+Na$^+$)
EXAMPLE 35
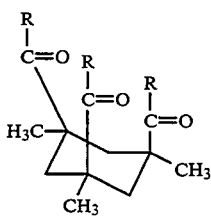
R =

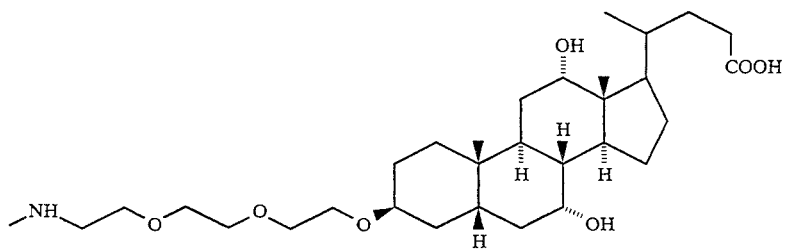

$C_{102}H_{171}N_3O_{24}$ (1822), MS (FAB, 3-NBA): 1823 (M+H+)

EXAMPLE 36

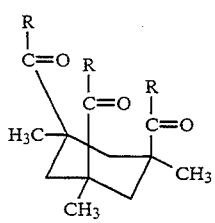

R =

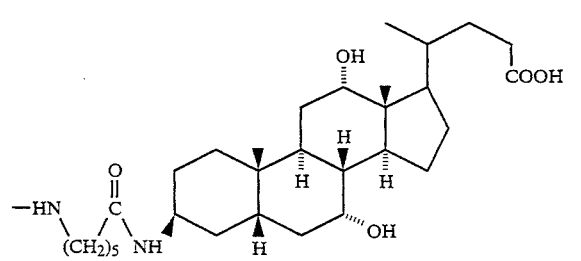

$C_{102}H_{168}N_6O_{18}$ (1765), MS (FAB, 3-NBA ): 1766 (M+H+)

EXAMPLE 37

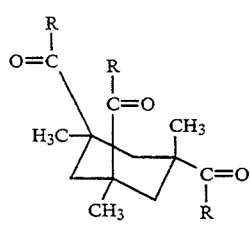

R =

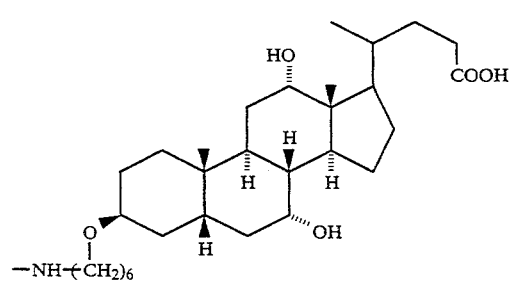

$C_{102}H_{171}N_3O_{18}$ (1726), MS (FAB, 3-NBA )=1727 (M+H+)

EXAMPLE 38

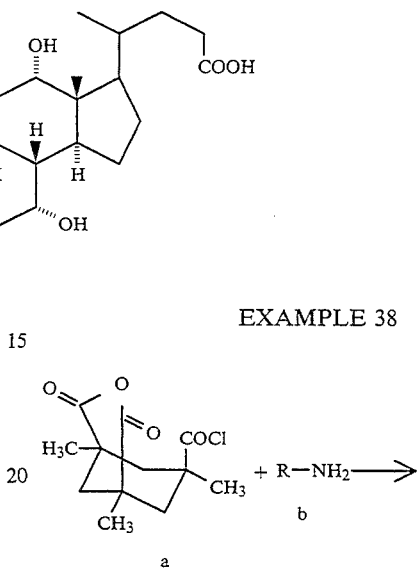

5.18 g (0.02 tool) of the acid derivative a are treated with ice-cooling with 21 g (0.04 tool) of amine b (dissolved in 150 ml of dichloromethane) in 350 ml of dry dichloromethane with the addition of 6 ml of triethylamine and, after addition is complete, stirred at room temperature for 6 h. The salt formed is filtered off, the filtrate is extracted by shaking several times with 2N citric acid and water and the residue which remains after drying and concentration is purified by colunm filtration on silica gel. 15.9 g ( 63% ) of compound c, "Example 38" are obtained.

$C_{74}H_{124}N_2O_{14}$ (1265), MS (FAB, 3-NBA): 1266 (M+H+)

EXAMPLE 39

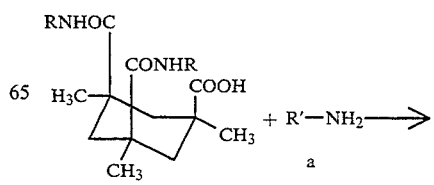

-continued

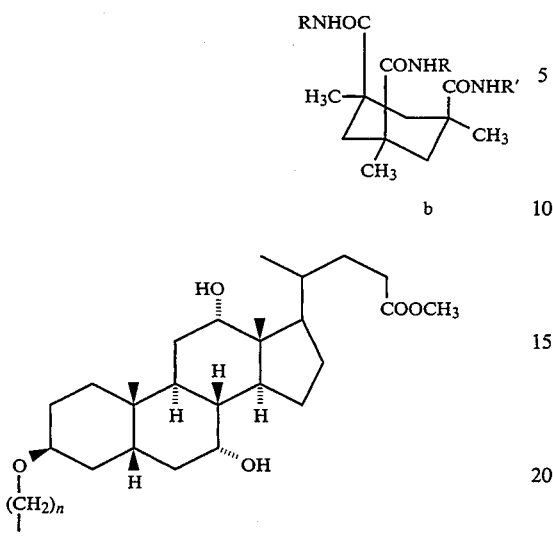

b mit n = 6: R
mit n = 2: R'

633 mg (0.5 mmol) of "Example 38" are dissolved in 30 ml of THF and activated with 70 mg (0.52 mmol) of hydroxybenzotriazole and 110 mg (0.53 mmol) of dicyclohexylcarbodiimide. 243 mg (0.52 mmol) of amine a are added and the mixture is stirred overnight at room temperature. It is then worked up as described under "Example 15". After chromatographic purification, 582 mg (60%) of product b are obtained.

$C_{101}H_{169}N_3O_{18}$ (1712), MS (FAB, 3-NBA): 1713 (M+H+)

EXAMPLE 40

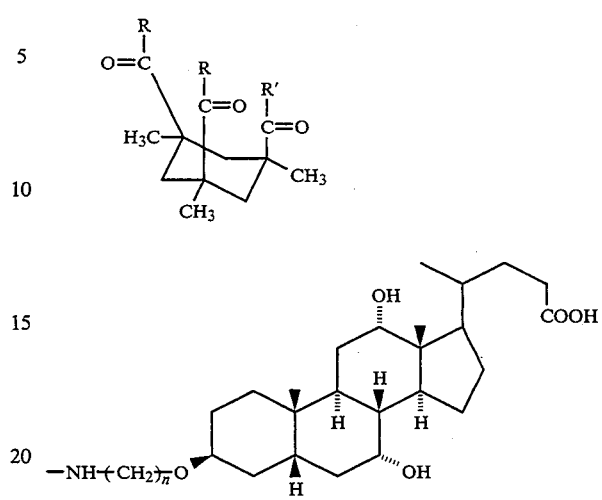

where n = 6: R
where n = 2: R'

The substance is prepared from "Example 39" by alkaline hydrolysis analogously to "Example 16".

$C_{98}H_{163}N_3O_{18}$ (1670), MS (FAB, 3-NBA): 1671 (M+H+)

EXAMPLE 41

R as in Example 40

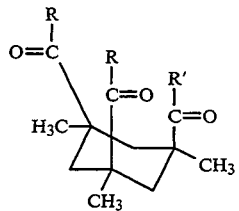

R' =

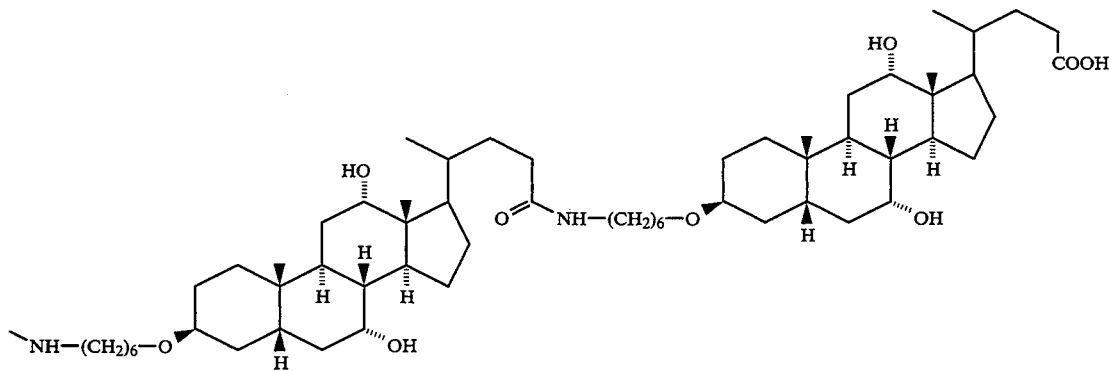

The substance is prepared analogously to "Example 40" using the dimeric amine corresponding to R'.

$C_{132}H_{222}N_4O_{22}$ (2216), MS (FAB, 3-NBA): 2217 (M+H+)

The following example substances are prepared analogously to the reactions described in Examples 15 and 16 using the corresponding oligocarboxylic acids and amines.

EXAMPLE 42

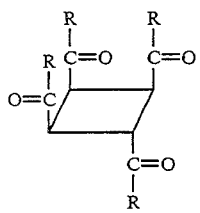

R =

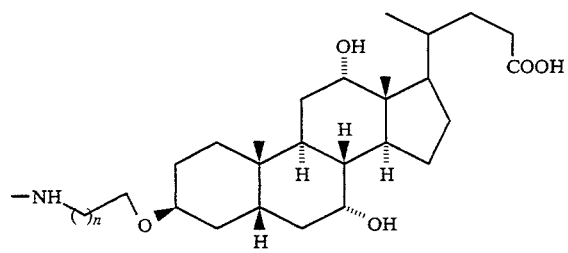

n = 1

$C_{112}H_{180}N_4O_{24}$ (1965), MS (FAB, 3-NBA): 1966 $(M+H^+)$

EXAMPLE 43

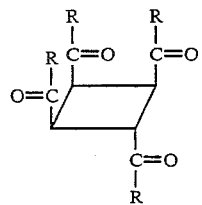

R =

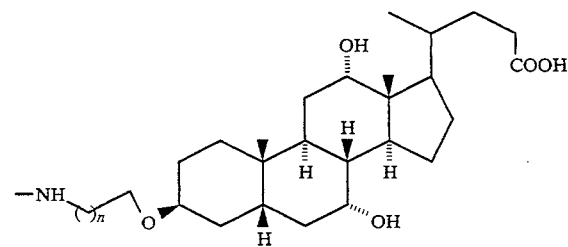

n = 5

$C_{128}H_{212}N_4O_{24}$ (2190), MS (FAB, 3-NBA): 2191 $(M+H^+)$

EXAMPLE 44

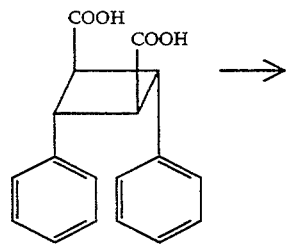

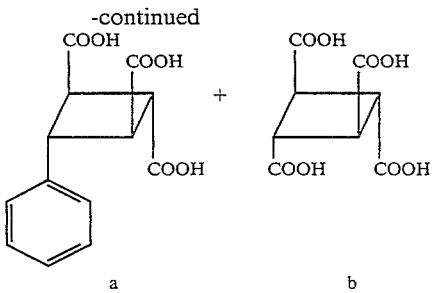

a    b

If the ozonolysis is stopped prematurely during the reaction of ε-truxillic acid to give trans,trans,trans-cyclobutane-1,2,3,4-tetracarboxylic acid (Chem. Ber. 83, 2521 (1960)), a product mixture is obtained after working up which can be separated by chromatography (silica gel, $CHCl_3/MeOH$ 6:1). The first fraction obtained is the novel 4-phenylcyclobutane-1,2,3-tricarboxylic acid (a), MS (FAB, 3-NBA) $C_{13}H_{12}O_6$ (264): 265 $(M+Li^+)$, the second fraction cyclobutane-1,2,3,4-tetracarboxylic acid (b).

The following example substances are prepared analogously to the reactions described in Examples 15 and 16 using the corresponding oligocarboxylic acids and amines.

EXAMPLE 45

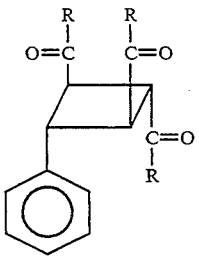

R =

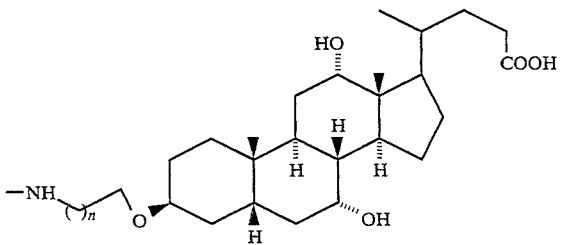

n = 1

$C_{91}H_{141}N_3O_{18}$ (1564), MS (FAB, 3-NBA): 1565 $(M+H^+)$

EXAMPLE 46

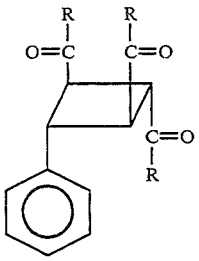

-continued

R =

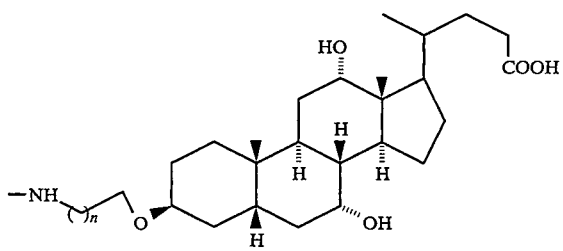

n = 5

C$_{103}$H$_{165}$N$_3$O$_{18}$ (1732), MS (FAB, 3-NBA); 1733 (M+H$^+$)

EXAMPLE 47

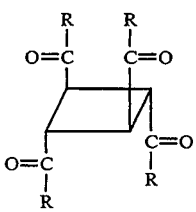

R =

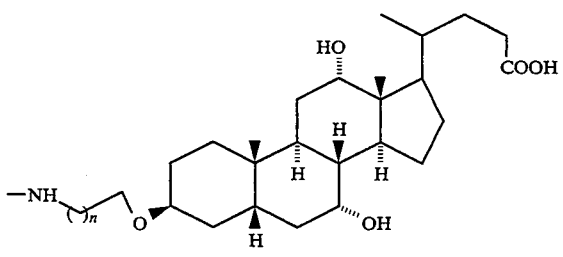

n = 1

C$_{112}$H$_{180}$N$_4$O$_{24}$ (1965), MS (FAB, 3-NBA): 1966 (M+H$^+$)

EXAMPLE 48

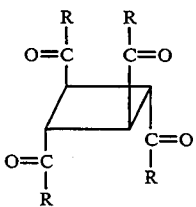

R =

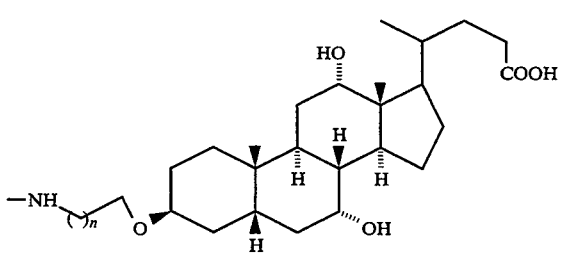

-continued n = 5

C$_{128}$H$_{212}$N$_4$O$_{24}$ (2190), MS (FAB, 3-NBA):2191 (M+H$^+$)

What is claimed is:

1. A bile acid derivative of the formula (I), $$Z(-X-GS)_n \qquad (I)$$

wherein GS is a radical of the formula (II),

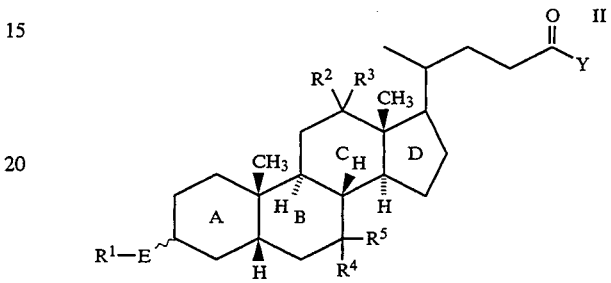

which is linked to X in 3-position and in which

E is a single bond, oxygen or NH,

Y is a free valency for bonding the group X or has one of the following meanings

—OL, —NHL—, —NL$_2$, an amino acid bonded via the amino group or an aminosulfonic acid, selected from the group consisting of

—NHCH$_2$—CO$_2$H,   —NH—CH$_2$CH$_2$—SO$_3$H,

—N—CH$_2$CH$_2$—SO$_3$H,
 |
 CH$_3$

—N—CH$_2$CO$_2$H,   —NH—CHCO$_2$H,
 |                    |
 CH$_3$                R$^6$ or the (C$_1$–C$_4$)-alkyl ester or alkali metal and alkaline earth metal salts of said acid, —OCat, where Cat is an alkali metal or alkaline earth metal ion or is a quaternary ammonium ion and where L is H, an alkyl or alkenyl radical having up to 10 carbon atoms, which is branched or unbranched, a cycloalkyl radical having 3 to 8 carbon atoms, a phenyl radical which is unsubstituted or substituted 1 to 3 times by F, Cl, Br, (C$_1$–C$_4$)-alkyl or (C$_1$–C$_4$)-alkoxyl, a benzyl radical, which is unsubstituted or substituted 1 to 3 times by F, Cl, Br, (C$_1$–C$_4$)-alkyl or (C$_1$–C$_4$)-alkoxy, and R$^6$ is methyl, isopropyl, isobutyl, 2-butyl, benzyl, 4-hydroxybenzyl, hydroxymethyl, 1-hydroxyethyl, H$_3$CSCH$_2$CH$_2$CH$_2$—, HO$_2$CCH$_2$—, HOCCH$_2$CH$_2$—, or Y is a free valency for bonding a further bile acid radical or modified bile acid radical via ring A thereof, the bonding taking place via a linker having the meaning of X, R$^1$ is a free valency for bonding the group X or H, an alkyl radical or alkenyl radical having up to 10 carbon atoms, which is branched or unbranched, a cycloalkyl radical having 3 to 8 carbon atoms, a phenyl radical which is unsubstituted or substituted 1 to 3 times by F, Cl, Br, $(C_1-C_4)$-alkyl or $(C_1-C_4)$-alkoxy, $-NH_3^{\oplus}$ $-OPO_3^{\ominus}$ a benzyl radical, which is unsubstituted in the ring or substituted 1 to 3 times by F, Cl, Br, $(C_1-C_4)$-alkyl, $(C_1-C_4)$-alkoxy, $-NH_3^{\oplus}$, $-OPO_3^{\ominus}$, or phenyl which in turn can be substituted 1 to 3 times by F, Cl, Br, $(C_1-C_4)$-alkyl or $(C_1-C_4)$-alkoxy, $-NH_3^{\oplus}$, $-OPO_3^{\ominus}$, a biphenylmethyl radical which is unsubstituted or substituted 1 to 3 times by F, Cl, Br, $(C_1-C_4)$-alkyl, $(C_1-C_4)$-alkoxy, $-NH_3^{\oplus}$, $-OPO_3^{\ominus}$, a triphenylmethyl radical which is unsubstituted or substituted by F, Cl, Br, $(C_1-C_4)$-alkyl, $(C_1-C_4)$-alkoxy, $-NH_3^{\oplus}$, $-OPO_3^{\ominus}$, a 1- or 2-naphthylmethyl radical, which is unsubstituted or substituted 1 to 3 times by F, Cl, Br, $(C_1-C_4)$-alkyl or $(C_1-C_4)$-alkoxy, $-NH_3^{\oplus}$, $-OPO_3^{\ominus}$, a 9-fluorenyl radical which is unsubstituted or substituted 1 to 3 times by F, Cl, Br, $(C_1-C_4)$-alkyl or $(C_1-C_4)$-alkoxy, $-NH_3^{\oplus}$, $-OPO_3^{\ominus}$, a 2-, 3- or 4-pyridyl radical,

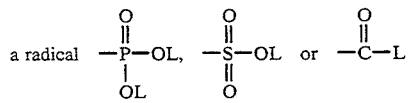

where L has the above-mentioned meaning, $R^2$ to $R^5$, where $R^2$ and $R^3$ or $R^4$ and $R^5$ in each case together are the oxygen of a carbonyl group, or individually and in each case independently of one another are

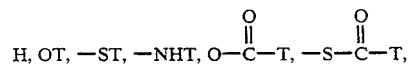

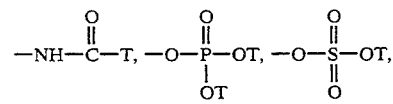

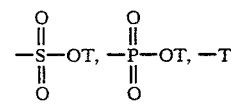

where T is hydrogen, alkyl having up to 10 carbon atoms, cycloalkyl having 3 to 8 carbon atoms, phenyl or tetrahydropyranyl;

X is a single bond or a group of the formula III

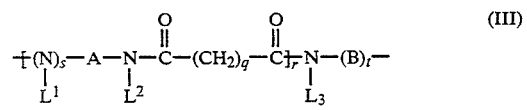

where

A is an alkylene chain which is branched or unbranched and can be optionally interrupted by —O—, —S— or phenylene in the chain, where the linkage

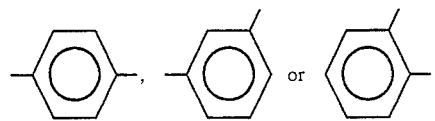

takes place and the chain altogether comprises 2 to 12 chain members p,

B is an alkylene chain, which is branched or unbranched and can be optionally interrupted by —O—, —S— or phenylene in the chain where the linkage

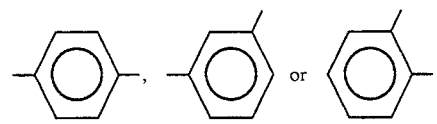

takes place and the chain altogether contains 2 to 18 chain members n, $L^1$, $L^2$ and $L^3$ are identical or different and have the meaning of L, q is 0 to 5, r is 0 or 1, s is 0 or 1, and t is 0 or 1, and wherein the central bridge group Z is an open-chain alkyl radical having up to 20 carbon atoms, the alkyl radical being straight-chain or branched and optionally being interrupted with up to 6 ether bridges, a cycloalkyl radical having 3 to 8 carbon atoms or a phenyl radical, said radical having 3 to 4

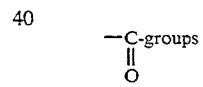

and being bonded to

X via —NH and where said radical is optionally substituted by $NH_2$, $NO_2$, $C_1-C_3$-alkyl, and n in the formula (I) is three or four.

2. The bile acid derivative of claim 1, wherein in formula (III), A is an alkylene chain which is branched or unbranched and can be optionally interrupted by —O—, —S— or phenylene in the chain, where the linkage

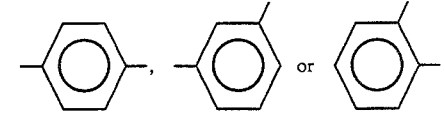

takes place and the chain altogether comprises 2 to 6 chain members p.

3. The bile acid derivative of claim 1, wherein in formula III, B is an alkylene chain, which is branched or unbranched and can be optionally interrupted by —O—, —S— or phenylene in the chain where the linkage

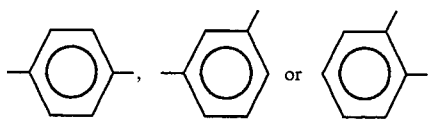

takes place and tile chain altogether contains 2 to 12 chain members n.

4. The bile acid derivative of claim 1, wherein in formula (III), $L^1$, $L^2$ and $L^3$ are identical or different and are hydrogen, $C_1$-$C_4$-alkyl or benzyl.

5. The bile acid derivative of claim 1, wherein in the central bridge group Z, said radical is substituted by methyl or phenyl.

6. A bile acid derivative as claimed in claim 1, wherein X is a single bond, or a radical of the formula III in which $L^1$, $L^2$ and $L^3$ are hydrogen, $C_1$-$C_4$-alkyl or benzyl, and the central bridge group Z is an open-chain alkyl radical having up to 20 carbon atoms, the alkyl radical being straight-chain or branched and optionally interrupted by up to 6 ether bridges, a cycloalkyl radical having 3 to 8 carbon atoms or a phenyl radical, said radicals having 3 to 4 —C=O groups and being bonded to X via NH and said radicals are optionally substituted by $NH_2$, $NO_2$, methyl or phenyl.

7. A pharmaceutical composition comprising a compound as claimed in claim 1 and a pharmaceutically acceptable carrier.

8. A hypolipidemic comprising a compound as claimed in claim 1.

* * * * *

UNITED STATES PATENT AND TRADEMARK OFFICE
CERTIFICATE OF CORRECTION

PATENT NO. : 5,428,182
DATED : June 27, 1995
INVENTOR(S) : Alfons ENHSEN et al

It is certified that error appears in the above-indentified patent and that said Letters Patent is hereby corrected as shown below:

Claim 1, Column 32, Line 53, "alkoxyl" should read --alkoxy--;

Claim 1, Column 32, Line 59, "$H_3CSCH_2CH_2CH_2$" should read --$H_3CSCH_2CH_2$--;

Claim 1, Column 33, Line 3, "--$NH_3^{\oplus}$--$OPO_3^{\ominus}$" should read -- -$NH_3^{\oplus}$, -$OPO_3^{\ominus}$--;

Claim 1, Column 33, Line 6, after "phenyl" insert --,--; and Column 34, Line 25 after "$L^2$" insert --,--.

Claim 3, Column 35, Line 9, "tile" should read --the--.

Signed and Sealed this

Sixteenth Day of July, 1996

Attest:

BRUCE LEHMAN

*Attesting Officer*     *Commissioner of Patents and Trademarks*